United States Patent
Jurek et al.

(10) Patent No.: US 10,450,673 B2
(45) Date of Patent: Oct. 22, 2019

(54) METHOD OF SYNTHESIS AND PURIFICATION OF A NUCLEOSIDE AND/OR A NUCLEOTIDE, A MODIFIED NUCLEOSIDE AND/OR NUCLEOTIDE, A DNA MOLECULE AND AN OLIGONUCLEOTIDE LIBRARY COMPRISING SAID MODIFIED NUCLEOSIDE AND/OR NUCLEOTIDE AND THE USE OF SAID OLIGONUCLEOTIDE LIBRARY

(71) Applicant: PURE BIOLOGICS SPOLKA AKCYJNA, Wroclaw (PL)

(72) Inventors: Przemyslaw Jurek, Lutynia (PL); Filip Jelen, Wroclaw (PL); Maciej Mazurek, Wroclaw (PL); Piotr Jakimowicz, Wroclaw (PL)

(73) Assignee: PURE BIOLOGICS SPOLKA AKCYJNA, Wroclaw (PL)

( * ) Notice: Subject to any disclaimer, the term of this patent is extended or adjusted under 35 U.S.C. 154(b) by 0 days.

(21) Appl. No.: 15/760,915

(22) PCT Filed: Sep. 13, 2016

(86) PCT No.: PCT/PL2016/050038
§ 371 (c)(1),
(2) Date: Mar. 16, 2018

(87) PCT Pub. No.: WO2017/048147
PCT Pub. Date: Mar. 23, 2017

(65) Prior Publication Data
US 2018/0265862 A1   Sep. 20, 2018

(30) Foreign Application Priority Data
Sep. 17, 2015   (PL) .................................... 413941

(51) Int. Cl.
*C40B 40/06*   (2006.01)
*C12N 15/115*   (2010.01)
(Continued)

(52) U.S. Cl.
CPC ............... *C40B 40/06* (2013.01); *C07H 1/00* (2013.01); *C07H 1/06* (2013.01); *C07H 19/06* (2013.01);
(Continued)

(58) Field of Classification Search
CPC . C07H 1/00; C07H 1/06; C07H 19/06; C07H 19/073; C07H 19/10; C07H 21/04;
(Continued)

(56) References Cited

FOREIGN PATENT DOCUMENTS

WO   WO2009/012363 A2   1/2009

OTHER PUBLICATIONS

Cheng et al., (2011), "Design, Synthesis, and Polymerase-Catalyzed Incorporation of Click-Modified Boronic Acid-TTP Analogues", Chemistry—An Asian Journal, vol. 6, Issue 10, Sep. 2, 2011, pp. 2747-2752.
(Continued)

*Primary Examiner* — Jeremy C Flinders
(74) *Attorney, Agent, or Firm* — ALGM LLP; Harry J. Guttman (57) ABSTRACT

The object of the invention is a method of synthesis and purification of a nucleoside and/or a nucleotide being a mono-, di- or triphosphate, wherein a Huisgen' s azide-alkyne cycloaddition reaction is being performed using a compound of structure (1) with a compound chosen from the group of structures (2) to (5). The object of the invention is also a modified nucleoside and/or nucleotide of structure (10), a DNA molecule and an oligonucleotide library com-
(Continued)

prising one or more modified nucleotides and the use of said oligonucleotide library for aptamers selection.

11 Claims, 7 Drawing Sheets

(51) Int. Cl.
| | |
|---|---|
| *C07H 1/00* | (2006.01) |
| *C07H 19/073* | (2006.01) |
| *C07H 19/10* | (2006.01) |
| *C07H 21/04* | (2006.01) |
| *C07H 1/06* | (2006.01) |
| *C07H 19/06* | (2006.01) |
| *C12N 15/10* | (2006.01) |

(52) U.S. Cl.
CPC ............ *C07H 19/073* (2013.01); *C07H 19/10* (2013.01); *C07H 21/04* (2013.01); *C12N 15/1048* (2013.01); *C12N 15/115* (2013.01); *C12N 2310/16* (2013.01)

(58) Field of Classification Search
CPC .............. C12N 15/1048; C12N 15/115; C12N 2310/16; C40B 40/06
See application file for complete search history.

(56) References Cited

OTHER PUBLICATIONS

Lee et al. "C5-Modified nucleosides exhibiting anticancer activity", Bioorganic & Medicinal Chemistry Letters vol. 19, Issue 16, Aug. 15, 2009, pp. 4688-4691.
Frank et al., "A 2'-deoxycytidine long-linker click adduct forming two conformers in the asymmetric unit," Acta Crystallographica, Section C: Crystal Structure Communications, 2012, 68(4), pp. 0174-0178.
Jitka et al., "Azidopropylvinylsulfonamide as a New Bifunctional Click Reagent for Bioorthogonal Conjugations: Application for DNA-Protein Cross-Linking", Chemistry—A European Journal (2015), 21(45), pp. 16091-16102.
Hai et al., "Cross-Linked DNA: Site-Selective "Click" Ligation in Duplexes with Bis-Azides and Stability Changes Caused by Internal Cross-Links", Bioconjugate Chemistry, 2012, 23(6), pp. 1230-1243.
International Search Report for PCT/PL2016/050038, dated Jan. 12, 2017.

Fig. 1A

Structure 6

Structure 7

Structure 8

Structure 9

Fig. 1B

Structure 10

METHOD OF SYNTHESIS AND PURIFICATION OF A NUCLEOSIDE AND/OR A NUCLEOTIDE, A MODIFIED NUCLEOSIDE AND/OR NUCLEOTIDE, A DNA MOLECULE AND AN OLIGONUCLEOTIDE LIBRARY COMPRISING SAID MODIFIED NUCLEOSIDE AND/OR NUCLEOTIDE AND THE USE OF SAID OLIGONUCLEOTIDE LIBRARY

The subject of the present invention is a method of synthesis and purification of a nucleoside and/or a nucleotide, a modified nucleoside and/or nucleotide, a DNA molecule and an oligonucleotide library comprising said modified nucleoside and/or nucleotide and use of said oligonucleotide library. The objects of the invention can be applied in in vitro selection of aptamers used as therapeutic molecules and also as basic components of molecular diagnostic tools.

Aptamers are oligonucleotides—single-stranded fragments of ribonucleic acid or deoxyribonucleic acid (RNA or DNA), usually from over ten to several tens of nucleotides in length, whose defined sequence allows them to conform a three-dimensional structure fitting to the molecular structure of the ligand and to bind said ligand with high sensitivity and selectivity. Aptamers present very numerous applications in biotechnology and medicine, both as therapeutic molecules and as basic components of molecular diagnostic tools. This leads to aptamers being often compared with widely used antibodies. However, the scope of potential ligands, towards which working aptamers have already been selected, is much broader than mostly protein-based partners of antibodies. Aptamers ligands also include low molecular weight compounds of almost any structure, such as e.g. metal ions, alkaloids, organic dyes, amino acids, nucleosides, nucleotides, porfirins or sugars[1-3]. Other aptamers advantages, which place them above antibodies in many applications, include: small size (the smallest selected working aptamer is 15 nucleotides in length[4], which corresponds to the mass of about 4600 g/mol); low or zero immunogenicity; cheap and efficient chemical synthesis, which also provides 100% homogenic preparation; the possibility of introducing various chemical modifications; strong resistance to non-physiological conditions and the ability of spontaneous renaturation, and relatively fast process of aptamers selection towards chosen molecular target.

Aptamers are obtained in a process of "in vitro evolution" called the SELEX method (Systematic Evolution of Ligands by EXponential enrichment). It is based on repetitive binding of a pool of oligonucleotide molecules with different sequences (usually $10^{12}$-$10^{14}$ molecules in the first round of selection) with a chosen molecular target, and subsequent physical partitioning of the molecules which have bound the target from the unbound molecules. After the partitioning the oligonucleotides binding the target are enzymatically amplified and the process is repeated, usually with more stringent conditions in order to select molecules of desired target binding parameters[5,6]. Aptamers obtained in such a way are subjected to sequencing—knowledge of the nucleotide sequence allows to chemically synthesize a pure aptamer for further use or for further optimization, comprising for example of introducing modifications or trimming of the oligonucleotide.

The libraries are sets of single-stranded nucleic acid molecules comprising in theirs sequences a region of random nucleotide sequence. During the SELEX process the sequences (clones) selected from the library are those sequences which exert the ability to bind a chosen molecular target, towards which the selection is being performed. Each nucleic acid molecule in the library has the same structure—two primer regions at both ends which enable the amplification of the library with Polymerase Chain Reaction (PCR), and a region with random sequence in the middle.

Both DNA and RNA are susceptible to digestion by nucleolytic enzymes. The use of aptamers in vivo or even in vitro in samples comprising nucleases (e.g. cell lysates) is hindered due to the degradation of nucleic acids by those enzymes. To overcome this problem many modifications to sugar-phosphate backbone of aptamers have been proposed, for example substituting the hydroxide group at 2' carbon with an amine group, or a substitution of one of the oxygen atoms in the phosphodiester bond with a sulfur atom (thio-aptamers). Another examples of methods reducing nucleic acids susceptibility to enzymatic digestion can be the introduction of "spiegelmers" oligonucleotides whose sugar backbone is composed of L-ribose isomer instead of naturally occurring D-isomer; or the employment of LNA (Locked Nucleic Acid)—an analogue in which ribose molecules have an additional bond connecting 4' carbon and 2' oxygen (thus closing' the ribose in 3'-endo conformation, which also influences the hybridization properties of the oligonucleotide).

A separate problem is a poor repertoire of monomers (nucleotides) of which the nucleic acids strands are formed in nature. The composition of naturally occurring nucleic acids includes only four different nucleobase molecules: adenine, guanine, cytosine and thymine (or uracil in the case of RNA), having only a few chemical groups which can take part in potential binding of the molecular target. It has generated a need of enriching the oligonucleotide libraries used for SELEX process with new unnatural nucleotides and chemical groups—analogues of naturally occurring nucleotides, which can help in selecting aptamers with better target binding properties. To meet this challenge many research groups have worked on enzymatic incorporation of modified nucleotides into the libraries and their use for selection[7-9].

In the state of art modified nucleotides are obtained by advanced organic synthesis methods, often long and multi-step processes with poor yield, not accessible for laboratories without special organic synthesis equipment[8-11]. Therefore, there is a need for easier, more efficient and quicker method of synthesis of modified nucleotides which may be further incorporated into nucleic acids using enzymatic methods, and said method will be useful in selection of new modified aptamers with better parameters than aptamers comprising only naturally occurring nucleotides.

Huisgen's Copper(I)-catalyzed Azide-Alkyne Cycloaddition (CuACC) enables a highly selective, efficient (often yields over 90%), quick (conjugation time can be less than an hour), run in mild-conditions (room temperature, normal pressure, broad selection of possible solvents including water, pH around 4 to 12), one-step conjugation of two compounds, one of which comprises a free azide group (—$N_3$), and the other a terminal alkyne (—C≡CH). The reaction is performed in the presence of copper (I) ions (a catalizator) and the resulting stable covalent triazol bond has always the same regioisometry[12,13]. For these reasons this reaction is classified as an example of so called "Click Chemistry"—a simple and "click"-like efficient conjugation chemistry with a broad application spectrum[14,15].

Authors of U.S. Pat. No. 6,175,001 (Barbas and Kandasamy, 2001)[10] describe preparation and use for DNA synthesis of nucleoside triphosphates bearing a modification in position 5 of deoxyuracil pyrimidine ring—it comprises a linker in the form of allylamine (prop-2-ene-1-amine) and a functional group attached to the linker through an amid bond. The functional groups used included benzoic acid, imidazole, pyridine, benzylamine or phenol. A series of organic synthesis reactions, in which from the initial compound 5-iododeoxyuridine the authors obtained a precursor for other modifications—5-(3-aminepropene)-deoxyuridine triphosphate, reached a yield of 24%. Next, the authors used this precursor compound to prepare modified nucleoside triphosphates with reactions, whose yield was 58-73%.

A publication "Expanding the chemistry of DNA for in vitro selection", Vaught et al., JAGS 2010, 132, 4141-4151 [9] discloses structures and a method of preparation of modified nucleoside triphosphates. The authors used 5-iododeoxyuridine in a palladium-catalyzed carboxyamidation reaction to prepare derivatives, whose functional groups (comprising benzyl, isobutane, methylnaphthalene, imidazol-4-ethane or (1H-indole-3-)ethane) are attached to carbon number 5 of pyrimidine ring with an amid bond. The conjugation reaction itself requires one step but lasts for 48-72 hours. It further requires prior substrate manipulation by introducing protective groups for hydroxyl groups in several reactions. The yield of the process has been presented by the authors as medium to good—from 30 to 60%. Next the authors have performed tests, in which they have shown that modified nucleotides are incorporated into DNA in a Primer Extension Reaction (PER) by DNA-dependent DNA polymerases (KOD XL, Pfu (exo-), D. Vent (exo-), Tth, Taq, KF (exo-)), and that the oligonucleotides comprising said modified nucleotides in their sequence can be also used as a template for PER. Modified nucleotides however couldn't be successfully used in a PCR.

In another publication "Synthesis of Deoxynucleoside Triphosphates that Include Proline, Urea, or Sulfonamide Groups and Their Polymerase Incorporation into DNA", Marcel Hollenstein, Chem. Eur. J. 2012, 18, 13320-13330 [16] the author presents synthesis and subsequent incorporation into DNA molecules of nucleotides enriched with complex functional groups (comprising proline residues, urea group, sulfamid group) attached to carbon number 5 of pyrimidine ring with a linker in the form of allylamine (prop-2-ene-1-amine) and an amid bond. Preparation of intermediate precursor from 5-iodouridine was performed with 31% yield. Next the precursor was used to synthesize five different nucleoside triphosphates—the series of synthesis reactions with the highest yield provided app. 23% conversion of the precursor into the product.

Presented methods of preparation of modified nucleotides require multiple reagents, specialized equipment for organic synthesis, they also characterize in low yield and multiple steps, which elongates the time of the preparation of the desired final compound.

The technical problem to be solved by the present invention is to propose such a method of synthesis of modified nucleotides and/or nucleosides, which would provide modified nucleotides and/or nucleosides that can be incorporated into nucleic acids by enzymatical methods, and thus they would be useful for selection of new modified aptamers with better parameters than aptamers comprising only naturally occurring nucleotides, wherein said method would not require using complicated and expensive specialized laboratory equipment and would be a process of high yield not requiring a prior substrate manipulation, and wherein said method would be relatively simple and quick, and the obtained product would be characterized by high purity level. Surprisingly, aforementioned technical problems and aims were provided by the present invention.

The first object of the invention is a method of synthesis and purification of a nucleoside and/or nucleotide, of which the substrate of structure 1 is a mono-, di- or triphosphate, characterized in that a Huisgen's azide-alkyne cycloaddition reaction is being performed using a compound of structure 1 with a compound of structure 2 or a compound of structure 3 or a compound of structure 4 or a compound of structure 5. In a preferred embodiment of the invention the Huisgen's azide-alkyne cycloaddition reaction is catalyzed by copper.

The second object of the invention is a modified nucleoside and/or a nucleotide being a mono-, di- or triphosphate, comprising cytosine or uracil as its nucleobase, which at position 5 of the heterocyclic ring has a 1,2,3-triazol group or an alkane or alkyne chain having a terminal 1,2,3-triazol group, and has a substituent at position 1 of said 1,2,3-triazol group which is a derivative of one of the compounds from the group of structures 2 to 5, and said modified nucleoside and/or nucleotide being of structure 10.

The third object of the invention is a DNA molecule comprising a single- or double-stranded DNA chain, characterized in that it comprises in one or more positions of the sequence of any or of both strands one or more modified nucleotides, as described in the second object of the invention. In a preferred embodiment of the invention the position of one or more modified nucleotides in the sequence is unrestricted. In another preferred embodiment the DNA molecule has been prepared by an enzymatic reaction (PCR, PER) or by chemical synthesis of oligonucleotides.

The fourth object of the invention is an oligonucleotide library having in its sequence a random sequence region of at least 10 nucleotides in length, and two flanking regions of constant sequences of at least 10 nucleotides in length, or deprived of flanking regions, characterized in that it comprises in one or more positions of the sequence one or more modified nucleotides, as described in the second object of the invention. In a preferred embodiment of the invention the position of one or more modified nucleotides in the sequence is unrestricted. In another embodiment of the invention the oligonucleotide library has been prepared by an enzymatic reaction (PCR, PER) or by chemical synthesis of oligonucleotides.

The fifth object of the invention is the use of the oligonucleotide library, as described in the fourth object of the invention, to obtain aptamers by SELEX technique and its derivatives.

The method of synthesis and purification of modified nucleotides and/or nucleosides according to the present invention allows preparing modified nucleotides and/or nucleosides, which can be incorporated into nucleic acids by enzymatic methods, thanks to which it is possible to use them in selection of new modified aptamers with better parameters than aptamers comprising only naturally occurring nucleotides. Presented method allowed to limit the number of steps of synthesis and purification in order to prepare modified nucleotides and/or nucleosides, wherein it didn't require the use of complex laboratory equipment. Synthesis and purification are characterized by high efficiency of the process, don't require prior substrate manipulation, are quick, and obtained products are characterized by high purity level. The enzymatic incorporation of the modified nucleotides into oligonucleotides is characterized by high efficiency, similar to the incorporation of naturally occurring nucleotides. Oligonucleotides described in the third object of the invention comprising modified nucleotides in their sequence are also characterized in that they can act as a template for PER or PCR, during which by the use of naturally occurring nucleotides there occurs a synthesis of unmodified oligonucleotides with sequences complementary to that of the template modified oligonucleotides—this requirement is necessary to be able to use the modified library for the selection of aptamers by SELEX technique and its derivatives, as described in the fifth object of the invention.

Example embodiments of the invention are presented by Examples and in the Figures, wherein.

EXAMPLE 1

Synthesis and Purification of a Modified Nucleotide of Structure 6

The synthesis reaction of nucleotide of structure 6 was prepared in 200 µl. To 4.0 µl of 100 mM EdUTP (5-ethynyl 2'-deoxyuridine 5'-triphosphate—structure 1.a).c).e); 400 nmol), 20 µl 10× TEAA buffer (triethylamine-acetic acid 500 mM pH 7.0) and 30 µl of DMSO-dissolved (S)-2-azido-3-methylbutyric acid (structure 2) at 200 mM concentration (6.0 µmol, 15 molar equivalents of EdUTP) were added. Next, 10 µl of previously prepared Cu-TBTA mixture (10 mM $CuSO_4$, 25 mM TBTA (tris[(1-benzyl-1H-1,2,3-triazol-4-yl)methyl]amine), 50% DMSO, 16,6% Cert-butanol) was added to final copper concentration in the reaction of 0.5 mM (0.25 molar equivalents of EdUTP). The mixture was filled up to 180 µl using DMSO, mixed, and 20 µl of sodium ascorbate at 200 mM concentration was added (to final concentration of 20 mM, 10 molar equivalents of EdUTP), thus initiating the reaction by reducing the copper to oxidation state, and the tube cap was tightly closed. A parallel negative control was prepared in 20 µl volume while maintaining the concentrations as in the positive sample, but with sodium ascorbate being replaced with deionized water. The reaction was conducted in a closed tube for 2 hours in 40° C. with vigorous shaking.

Figure 1A:
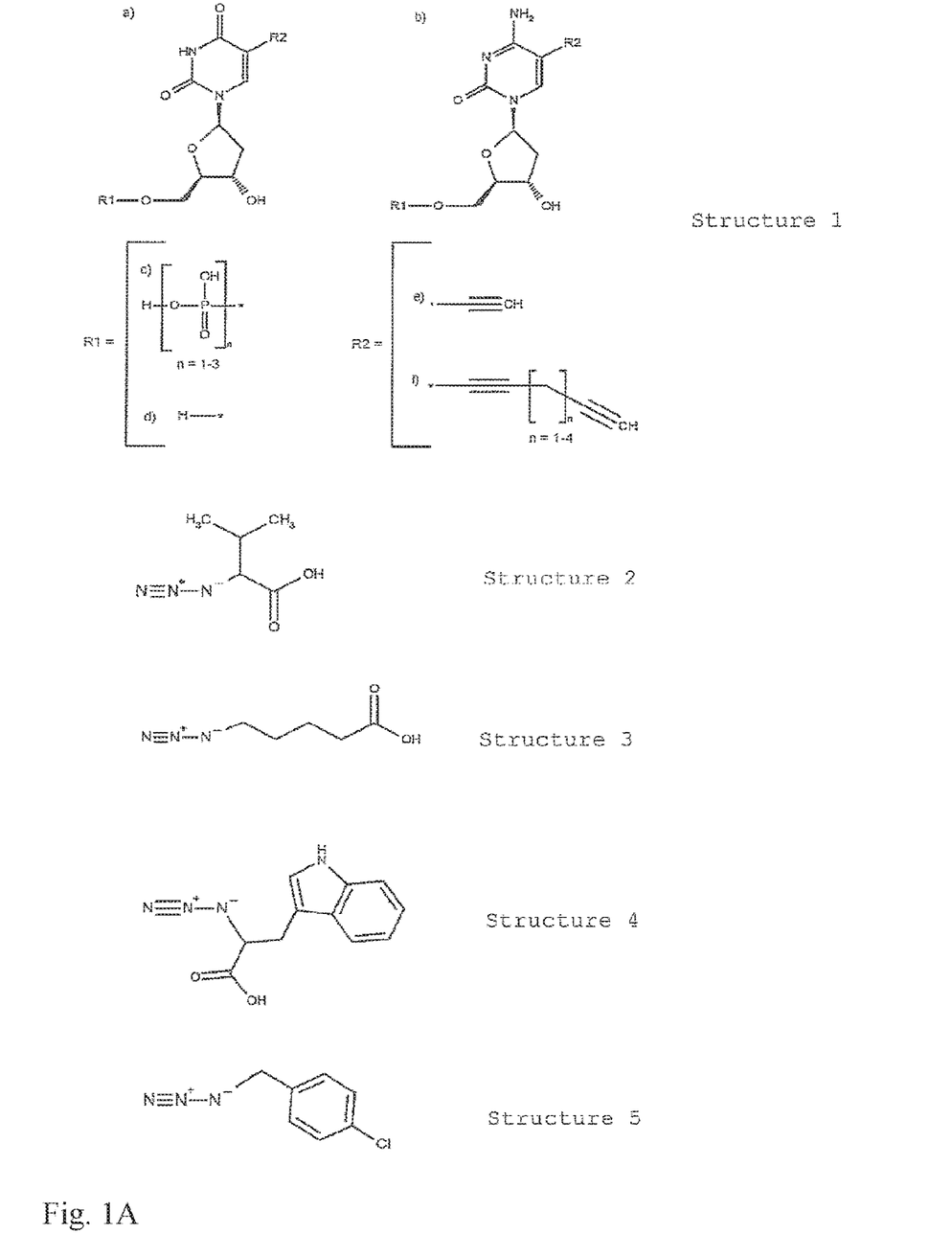
FIG. 1A presents structures 1-5.
Figure 1B:
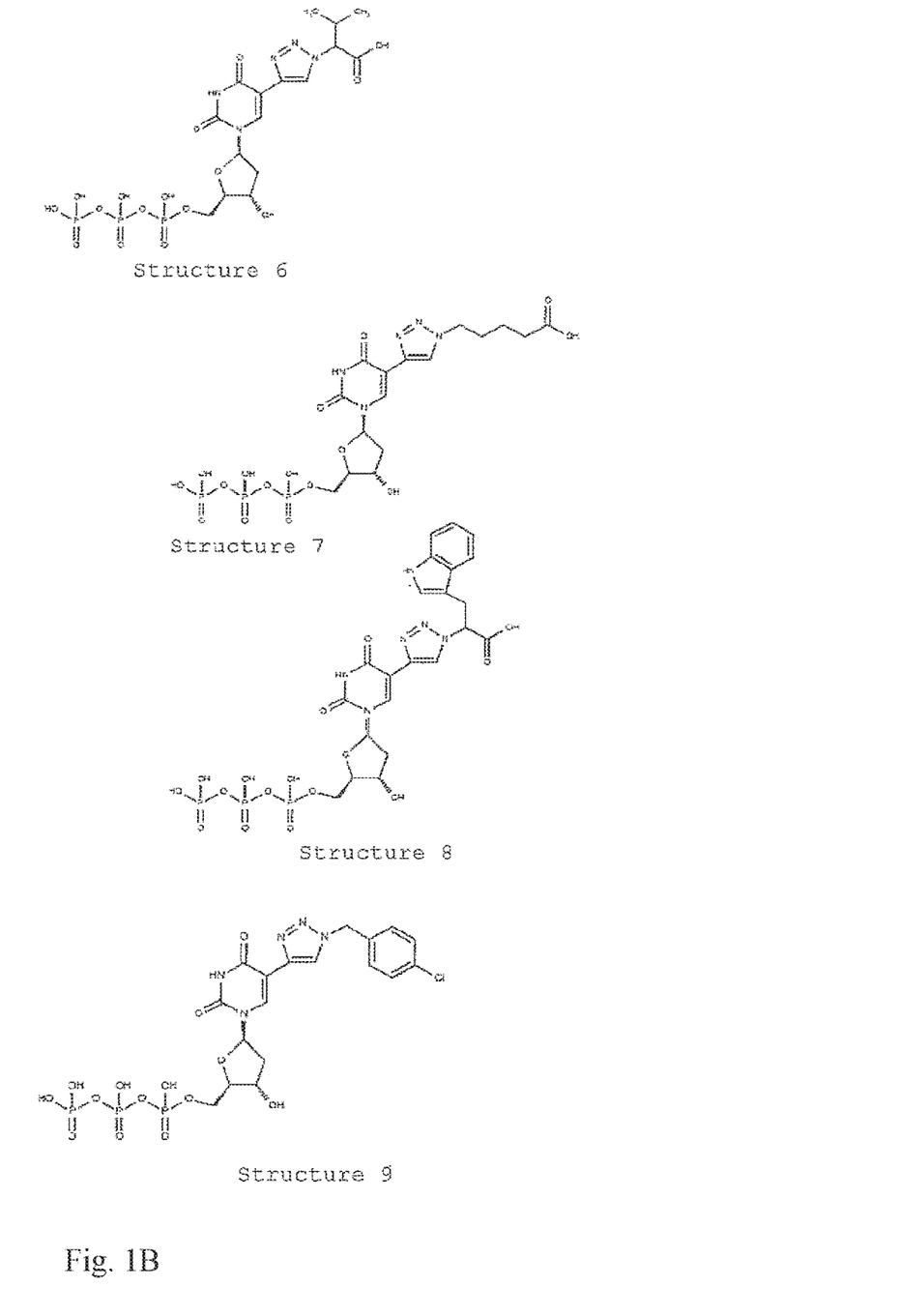
FIG. 1B presents structures 6-9.
Figure 1C:
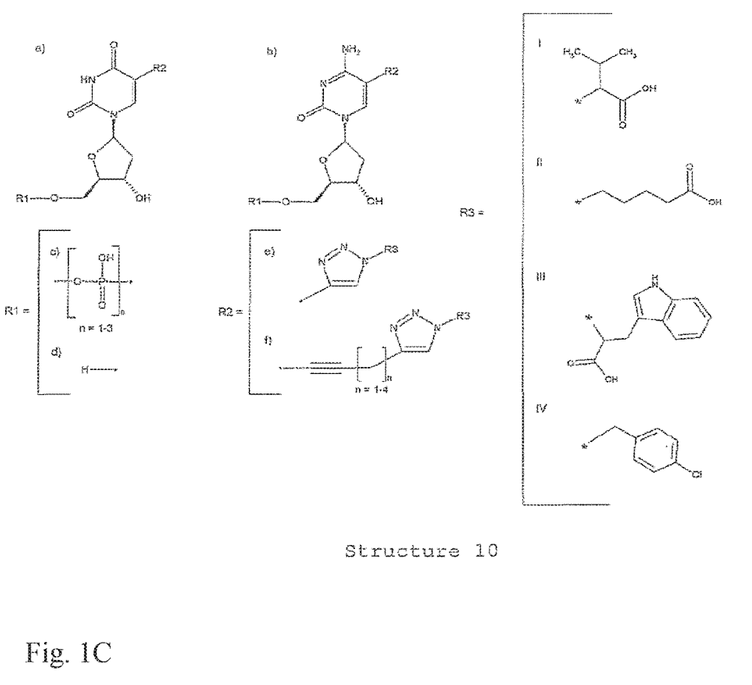
FIG. 1C presents structure 10.
Figure 1D:
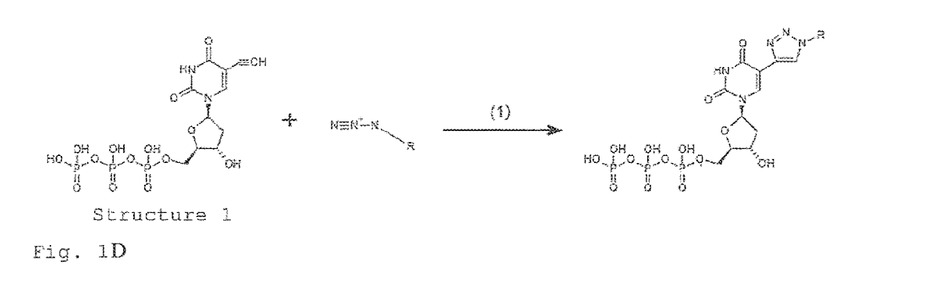
FIG. 1D presents an overall scheme of the Huisgen's copper-catalyzed azide-alkyne cycloaddition reaction.
Figure 2:
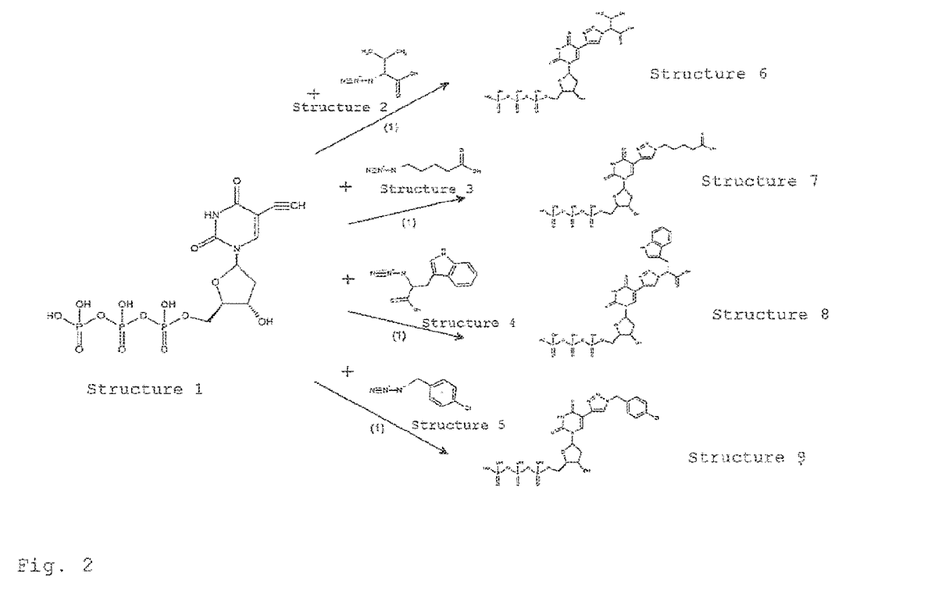
FIG. 2 presents schemes of reactions according to the present invention.
Figure 3:
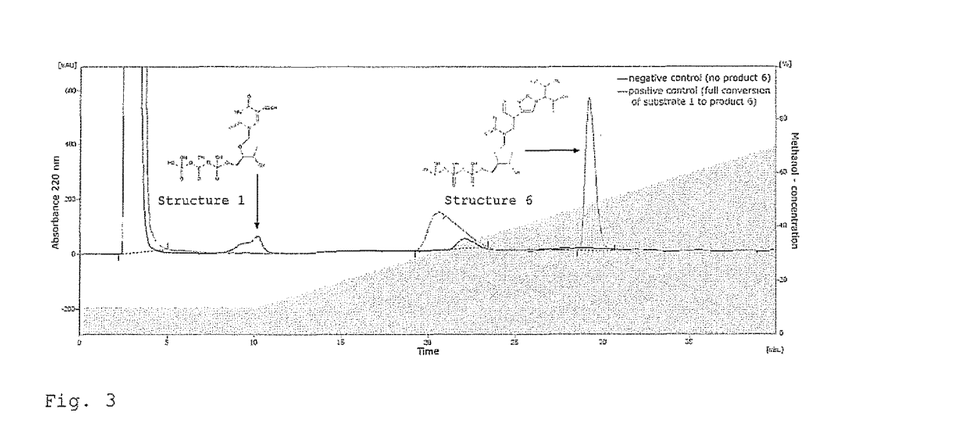
FIG. 3 presents a chromatogram of the nucleotide of structure 6 prepared by reversed-phase chromatography.
Figure 4:
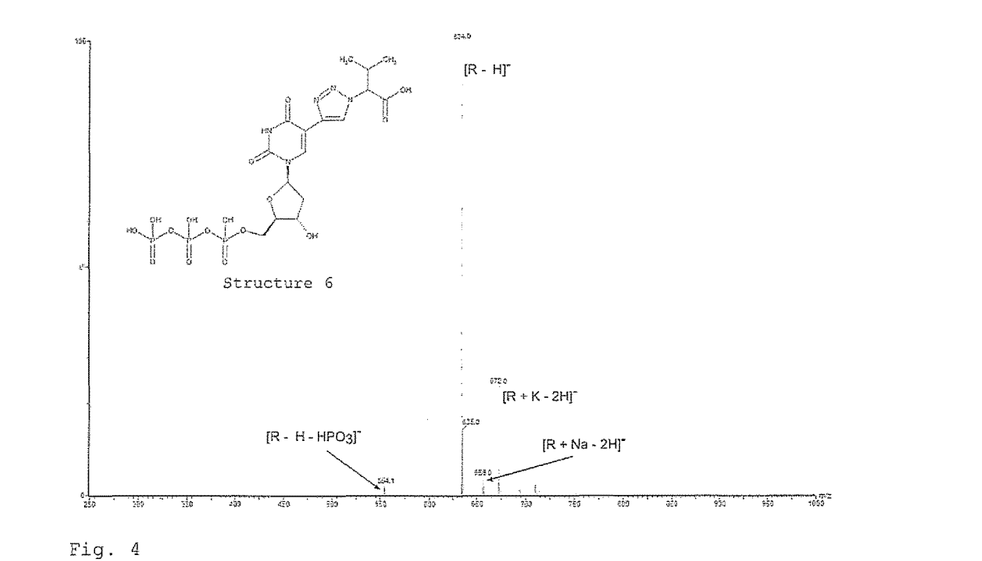
FIG. 4 presents a representative mass spectrum of the nucleotide of structure 6 obtained by mass analysis with MS-TOF (Mass Spectrometry—Time Of Flight)

Next the product was purified by reversed-phase chromatography, using TEAA 100 mM buffer and methanol as mobile phase (Bio-Rad's NGC chromatography system, Water's column AccQ-Tag, 60 Å, 4 µm, 3,9 mm×150 mm). The chromatogram of the analysis both from the negative control and the positive sample is presented in FIG. 3. Collected fractions containing the purified nucleotide of structure 6 were combined, dried in a vacuum concentrator (Labconco's CentriVap Benchtop Centrifugal Vacuum Concentrator) and dissolved in known volume of 25% DMSO. Next the sample was analyzed by MS-TOF (Water's Xevo G2-XS QTof spectrometer) in negative mode electrospray ionization: detected mass 634.04 Da, calculated mass 634.30 Da. A representative mass spectrum is presented in FIG. 4.

EXAMPLE 2

Synthesis and Purification of Modified Nucleotides of Structure 7-9

The synthesis reaction of nucleotides of structures 7-9 were performed analogically to the synthesis of compound of structure 6 (Example 1) using corresponding azides of structures 3-5 instead of compound of structure 2. Reaction temperature 40-55° C., reaction time 1-6 hours.

Mass analysis of products of structures 7-9: nucleotide of structure 7: detected mass 634.04 Da, calculated mass 634.30 Da; nucleotide of structure 8: detected mass 721.0 Da, calculated mass 721.38 Da; nucleotide of structure 9: detected mass 658.50 Da, calculated mass 658.75 Da.

EXAMPLE 3

Enzymatic Synthesis of Single-Stranded DNA Using Modified Nucleotide

Figure 5:
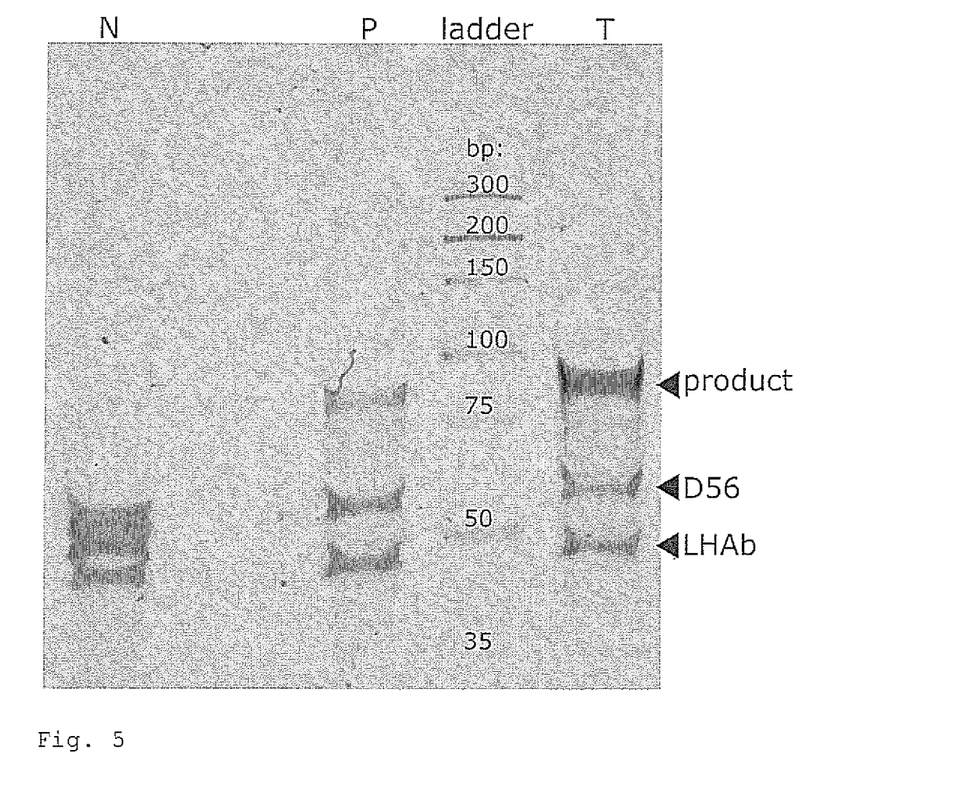
FIG. 5 presents the electrophoretic analysis result (an electropherogram) of the product of the enzymatic synthesis of an oligonucleotide comprising modified nucleotides of structure 9 in its sequence.

The enzymatic synthesis of an oligonucleotide comprising modified nucleotides of structure 9 in its sequence was performed in 10 µl volume using single-stranded template D56 (SEQ ID NO: 1) and primer LHAb (SEQ ID NO: 2; a polyA chain attached to 5'-end of the primer allows to discriminate the template from the product by mass) in a PER process. The reaction mixture was prepared, containing D56 at 2 µM concentration, LHAb at 4 µM concentration, Two polymerase 0.5 U, 1× concentrated buffer with magnesium supplied by the polymerase vendor, deionized water, and nucleotide triphosphates: dATP, dCTP and dGTP at final 200 µM concentration each. The negative control (sample N) did not contain any other nucleotides, the positive control (sample P) contained additionally TTP at 100 pM concentration, and the test sample (sample T) contained additionally the nucleotide of structure 9 (prepared as in Example 2) in 10× dilution. The reaction mixtures were incubated for one minute in 95° C., two minutes in 50° C. and 30 minutes in 70° C. After the reaction the samples were subjected to electrophoresis in a denaturing (7 M urea) 10% polyacrylamide gel (acrylamide 19:1 bis-acrylamide) heated to 55° C. with constant voltage of 300 V. The gel was visualized using Midori Green stain (Nippon Genetics)—FIG. 5.

Analogical experiments were performed for nucleotides of structures 6-8 confirming their proper incorporation into DNA by PER reaction. Obtaining of the product was also confirmed with other polymerase—DeepVent(exo-), as well as with different templates than D56 oligonucleotide.

The capability of DNA synthesis by Pwo polymerase on a biotinylated template immobilized on magnetic microbeads coated with streptavidin was also confirmed, accordingly with previous reports[9].

EXAMPLE 4

Enzymatic Synthesis of Single-Stranded DNA Library Comprising Modified Nucleotides in its Random Region The synthesis of single-stranded DNA library was performed with PER reaction analogically to Example 3, with explicit changes: unmodified library (SEQ ID NO: 3) was used as template, L4 primer was used as primer (SEQ ID NO: 4).

Single-stranded library comprising modified nucleotide or nucleotides of structures 6, 7, 8, or 9 was prepared by separating the strands of double-stranded product using magnetic microbeads coated with streptavidin, accordingly with previous reports[9], and its purity was assessed by electrophoresis (as in Example 3).

Another method to obtain single-stranded library comprising modified nucleotide or nucleotides of structures 6, 7, 8, or 9, is to separate the strands of double-stranded product in a denaturing (7 M urea) 10% polyacrylamide gel (acrylamide 19:1 bis-acrylamide) heated to 55° C. with constant voltage of 300 V. The gel was visualized using Midori Green stain, next the bands corresponding to the modified strand were cut out and they were subjected to purification procedure according to standard protocols.

Example 5

Enzymatic Synthesis of Unmodified Single-Stranded DNA Using a Template Comprising Modified Nucleotides in its Sequence Using a purified single-stranded oligonucleotide complementary to SEQ ID NO: 1 as a template which comprised modified nucleotides of structure 6 in its sequence (prepared as in Example 3 and purified from a polyacrylamide gel according to standard protocols); enzymatic synthesis of unmodified single-stranded DNA was performed (the product of the reaction is a reconstructed oligonucleotide D56 of SEQ ID NO: 1). The reaction was performed in 20 µl using a template described above and L4 primer (SEQ ID NO: 4) in a PER process. The reaction mixture was prepared, containing template at 0.1-2.0 µM concentration, L4 at 2-5 µM concentration, DeepVent polymerase 1 U or Pwo polymerase 1 U, 1× concentrated buffer supplied by the polymerase vendor (adequate to the polymerase used), magnesium sulfate at 2.0 mM, nucleotide triphosphates TTP, dATP, dCTP and dGTP at final 400 µM concentration each, and deionized water. The negative control (sample N) was not subjected to incubation (incubated at 4° C.) The test sample 1 (sample T1) was incubated for one minute in 95° C., one minute in 50° C. and 60 minutes in 70° C. The test sample 2 (sample T2) was subjected to 10 incubation cycles: for one minute in 95° C., one minute in 50° C. and 20 minutes in 70° C.

Figure 6:
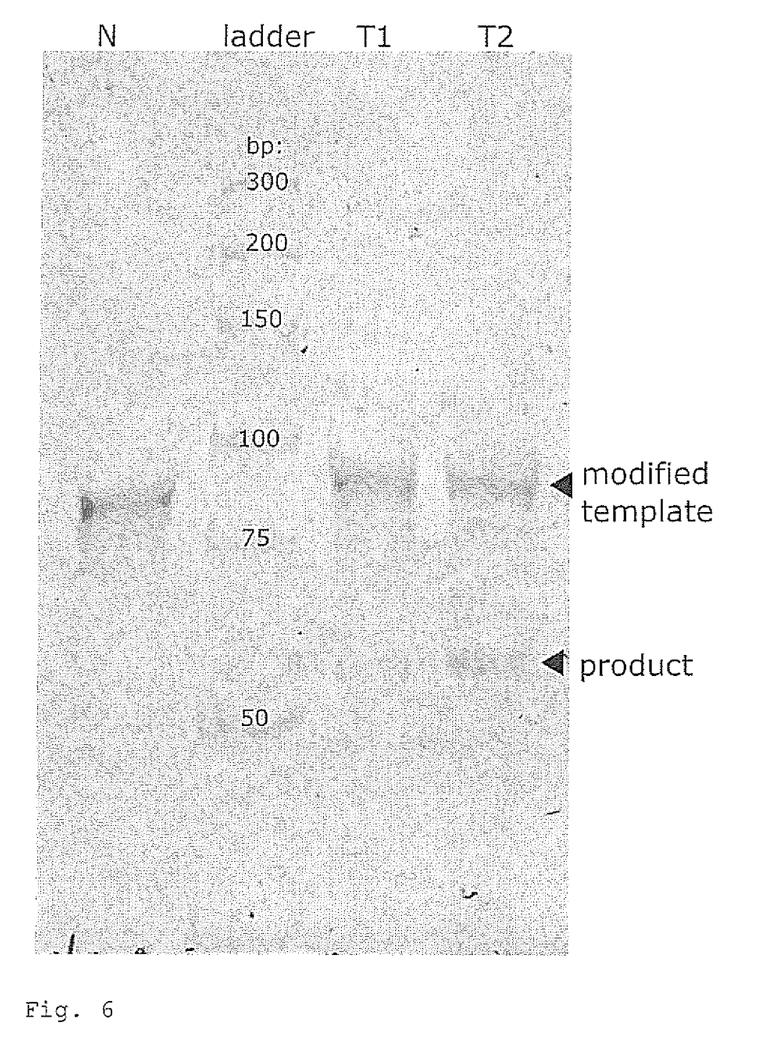
FIG. 6 presents the electrophoretic analysis result of the product of the enzymatic synthesis of an unmodified oligonucleotide, for which the template during the synthesis reaction was an oligonucleotide comprising modified nucleotides of structure 6 in its sequence.

After the reaction the samples were subjected to electrophoresis in a denaturing (7 M urea) 10% polyacrylamide gel (acrylamide 19:1 bis-acrylamide) heated to 55° C. with constant voltage of 300 V. The gel was visualized using Midori Green stain—FIG. 6.

Analogical experiments were performed with oligonucleotide templates comprising modified nucleotides of structure 7, 8, or 9 in their sequences.

REFERENCES

1. Famulok, M. Oligonucleotide aptamers that recognize small molecules. *Curr. Opin. Struct. Biol.* 1999, 9, 324-329.

2. Mayer, G. The Chemical Biology of Aptamers. *Angew. Chem. Int. Ed.* 2009, 48, 2672-2689.

3. Radom, F.; Jurek, P. M.; Mazurek, M. P.; Otlewski, J.; Jeleń, F. Aptamers: Molecules of great potential. *Biotechnol. Adv.* 2013.

4. Bock, L. C.; Griffin, L. C.; Latham, J. A.; Vermaas, E. H.; Toole, J. J. Selection of single-stranded DNA molecules that bind and inhibit human thrombin. *Nature* 1992, 355, 564-566.

5. Klug, S. J.; Famulok, M. All you wanted to know about SELEX. *Mol. Biol. Rep.* 1994, 20, 97-107.

6. Gold, L.; Tuerk, C. Nucleic Acid Ligands 1995.

7. Capek, P.; Cahová, H.; Pohl, R.; Hocek, M.; Gloeckner, C.; Marx, A. An efficient method for the construction of functionalized DNA bearing amino acid groups through cross-coupling reactions of nucleoside. triphosphates followed by primer extension or PCR. *Chem. Weinh. Bergstr. Ger.* 2007, 13, 6196-6203.

8. Schoetzau, T.; Langner, J.; Moyroud, E.; Roehl, I.; Vonhoff, S.; Klussmann, S. Aminomodified Nucleobases: Functionalized Nucleoside Triphosphates Applicable for SELEX. *Bioconjug. Chem.* 2003, 14, 919-926.

9. Vaught, J. D.; Bock, C.; Carter, J.; Fitzwater, T.; Otis, M.; Schneider, D.; Rolando, J.; Waugh, S.; Wilcox, S. K.; Eaton, B. E. Expanding the chemistry of DNA for in vitro selection. *J. Am. Chem. Soc.* 2010, 132, 4141-4151.

10. Barbas, C. F.; Kandasamy, S. Functionalized pyrimidine nucleosides and nucleotides and DNA's incorporating same 2001.

11. Gourlain, T.; Sidorov, A.; Mignet, N.; Thorpe, S. J.; Lee, S. E.; Grasby, J. A.; Williams, D. M. Enhancing the catalytic repertoire of nucleic acids. II. Simultaneous incorporation of amino and imidazolyl functionalities by two modified triphosphates during PCR. *Nucleic Acids Res.* 2001, 29, 1898-1905.

12. Himo, F.; Lovell, T.; Hilgraf, R.; Rostovtsev, V. V.; Noodleman, L.; Sharpless, K. B.; Fokin, V. V. Copper(I)-Catalyzed Synthesis of Azoles. DFT Study Predicts Unprecedented Reactivity and Intermediates. *J. Am. Chem. Soc.* 2005, 127, 210-216.

13. Rostovtsev, V. V.; Green, L. G.; Fokin, V. V.; Sharpless, K. B. A stepwise huisgen cycloaddition process: copper (I)-catalyzed regioselective "ligation" of azides and terminal alkynes. *Angew. Chem. Int. Ed Engl.* 2002, 41, 2596-2599.

14. Kolb, H. C.; Sharpless, K. B. The growing impact of click chemistry on drug discovery. *Drug Discov. Today* 2003, 8, 1128-1137.

15. Kolb, H. C.; Finn, M. G.; Sharpless, K. B. Click Chemistry: Diverse Chemical Function from a Few Good Reactions. *Angew. Chem. Int. Ed Engl.* 2001, 40, 2004-2021.

16. Hollenstein, M. Synthesis of deoxynucleoside triphosphates that include proline, urea, or sulfonamide groups and their polymerase incorporation into DNA. *Chem. Weinh. Bergstr. Ger.* 2012, 18, 13320-13330.

Sequence List:

SEQ ID NO: 1 - D56

SEQ ID NO: 2 - LHAb primer

SEQ ID NO: 3 - library

SEQ ID NO: 4 - L4 primer

The invention claimed is:

1. A method of synthesis and purification of a nucleoside and/or a nucleotide being a mono-, di- or triphosphate, characterized in that a Huisgen's azide-alkyne cycloaddition reaction is performed using compound of structure 1:

Structure 1 a)

-continued b)

where:

n = 1-3 with a compound of structure 2:

Structure 2 or with a compound of structure 3:

Structure 3 or with a compound of structure 4:

Structure 4 or with a compound of structure 5:

Structure 5

2. The method according to claim 1, wherein the Huisgen's azide-alkyne cycloaddition reaction is catalyzed by copper.

3. A modified nucleoside and/or a nucleotide being a mono-, di- or triphosphate, comprising cytosine or uracil as its nucleobase, which at position 5 of the heterocyclic ring has a 1,2,3-triazol group or an alkane or alkyne chain having a terminal 1,2,3-triazol group, and has a substituent at position 1 of said 1,2,3-triazol group which is a derivative of one of the compounds from the group of structures 2 to 5, and said modified nucleoside and/or nucleotide is of structure 1:

Structure 1 where:

n = 1-3 n = 1-4

4. A DNA molecule composed of a single- or double-stranded DNA chain, wherein it comprises in one or more positions of the sequence of any or both of the strands one or more modified nucleotides of claim 3.

5. The DNA molecule according to claim 4, wherein the position of one or more modified nucleotides is unrestricted.

6. The DNA molecule according to claim 4, wherein it has been prepared by an enzymatic reaction PCR, PER, or by the means of chemical synthesis of oligonucleotides.

7. A library of oligonucleotides comprising in its sequence a region with a random sequence at least 10 nucleotides in length, and two flanking regions with constant sequences at least 10 nucleotides in length, or deprived of the flanking regions, wherein it comprises in one or more positions of the sequence one or more modified nucleotides of claim 3.

8. The library according to claim 7, wherein the position of one or more modified nucleotides in the sequence is unrestricted.

9. The library according to claim 7, wherein it has been prepared by an enzymatic reaction PCR, PER, or by the means of chemical synthesis of oligonucleotides.

10. A method for producing one or more aptamers comprising
(a) contacting the library of oligonucleotides of claim 7 with a molecular target,
(b) separating oligonucleotides that are not bound to the molecular target from oligonucleotides that are bound to the molecular target,
(c) amplifying the oligonucleotides that are bound to the molecular target, and
(d) optionally repeating steps (a)-(c) one or more times.

11. The method of claim 10, wherein the amplifying comprises using PER or PCR.

* * * * *